(12) United States Patent
Kokai et al.

(10) Patent No.: US 9,327,012 B2
(45) Date of Patent: May 3, 2016

(54) COMPOSITION FOR TREATING, IMPROVING, OR PREVENTING PAIN

(75) Inventors: Yasuo Kokai, Sapporo (JP); Gousuke Ooki, Sapporo (JP); Kayo Matsumoto, Sapporo (JP); Shinichi Imai, Sapporo (JP); Takuro Wada, Sapporo (JP)

(73) Assignee: SAPPORO MEDICAL UNIVERSITY, Sapporo-shi, Hokkaido (JP)

( * ) Notice: Subject to any disclaimer, the term of this patent is extended or adjusted under 35 U.S.C. 154(b) by 39 days.

(21) Appl. No.: 14/001,212

(22) PCT Filed: Feb. 23, 2012

(86) PCT No.: PCT/JP2012/054408
§ 371 (c)(1),
(2), (4) Date: Nov. 4, 2013

(87) PCT Pub. No.: WO2012/115185
PCT Pub. Date: Aug. 30, 2012

(65) Prior Publication Data
US 2014/0057845 A1    Feb. 27, 2014

(30) Foreign Application Priority Data

Feb. 23, 2011    (JP) .................................. 2011-036855

(51) Int. Cl.
| | | |
|---|---|---|
| A61K 38/17 | (2006.01) | |
| C07K 14/825 | (2006.01) | |
| A61K 31/713 | (2006.01) | |
| G01N 33/68 | (2006.01) | |
| A61K 38/00 | (2006.01) | |
| A61K 48/00 | (2006.01) | |

(52) U.S. Cl.
CPC ............... *A61K 38/17* (2013.01); *A61K 31/713* (2013.01); *C07K 14/825* (2013.01); *G01N 33/6896* (2013.01); *A61K 38/00* (2013.01); *A61K 48/005* (2013.01); *G01N 2333/825* (2013.01); *G01N 2800/2842* (2013.01); *G01N 2800/52* (2013.01)

(58) Field of Classification Search
CPC ...................................................... A61K 38/00
See application file for complete search history.

(56) References Cited

U.S. PATENT DOCUMENTS 5,360,893 A *  11/1994  Owens et al. .................. 530/350
5,814,480 A     9/1998  Hillman et al.
6,271,196 B1 *  8/2001  O'Brien ........................ 514/18.3

FOREIGN PATENT DOCUMENTS

JP    2001-509026 A    7/2001
JP    2002-253250 A    9/2002

OTHER PUBLICATIONS

Roger S. Chung et al., "Redefining the Role of Metallothionein within the Injured Brain Extracellular Metallothioneins Play an Important Role in the Astrocyte-Neuron Response to Injury" Journal of Biological Chemistry, 2008, No. 22, pp. 15349-15358, vol. 283, No. 22.
Roger S. Chung et al., "The Native Copper-and-Zinc-Binding Protein Metallothionein Blocks Copper-Mediated Aβ Aggregation and Toxicity in Rat Cortical Neurons", PLoS One, Aug. 2010, pp. 1-11, vol. 5, issue 8.
Seiichi Nagano et al., "Reduction of Metallothioneins promotes the disease expression of familial amyotrophic lateral sclerosis mice in a dose-dependent manner", European Journal of Neuroscience, 2001, pp. 1363-1370, vol. 13.
Pedersen, M.O. et al., Biofactors, 2009, pp. 315-325, vol. 35, issue 4.
Manuchair Ebadi, M. et al., "Parkinson Disease", Experimental Biology and Medicine (Maywood), 2006, pp. 1576-1583, vol. 231, No. 9.
Roger S. Chung et al., "Metallothionein-IIA Promotes Initial Neurite Elongation and Postinjury Reactive Neurite Growth and Facilitates healing after Focal Cortical Brain Injury", Journal of Neuroscience, Apr. 2003, pp. 3336-3342, vol. 23, No. 8.
Roger Kevin Stankovic, et al.,"Decreased neurofilament density in large myelinated axons of metallothionein-I, II knockout mice", Neuroscience Letters, 2006, pp. 1-6, vol. 402, issues 1-2.
Gunnar F. Nordberg, "Historical perspectives on cadmium toxicology", Toxicology and Applied Pharmacology, 2009, pp. 192-200, vol. 238, No. 3.
Shun'Chi Horiguchi, Jukinzoku Chudoku, Karada no Kagaku Zokan, 1988, vol. 20, pp. 148-152.
Merck Manual 18th edition, Japanese language edition, Supervised by Masanori Fukushima, Nikkei Business Publications, Inc., 2006, pp. 2838-2866.
Iwao Uchiyama, "Metals as Potential Environmental Pollutants and their Health Effects", Materia Japan, 2004, pp. 636-638, vol. 43, No. 8.
International Search Report for PCT/JP2012/054408 Dated Apr. 17, 2012.

* cited by examiner

*Primary Examiner* — Karlheinz R Skowronek
*Assistant Examiner* — Li Lee
(74) *Attorney, Agent, or Firm* — Sughrue Mion, PLLC (57) ABSTRACT

In order to provide a composition for treating, improving, or preventing pain, it has been found out that a metallothionein protein is expressed in a normal peripheral nerve, and that the expression is not observed in a peripheral nerve producing pain. Moreover, it has been found out that administering metallothionein to rats having neuropathic pain suppresses the pain in the rats.

3 Claims, 6 Drawing Sheets
(5 of 6 Drawing Sheet(s) Filed in Color)

```
SEQUENCE LISTING

<160> NUMBER OF SEQ ID NOS: 2

<210> SEQ ID NO 1
<211> LENGTH: 28
<212> TYPE: DNA
<213> ORGANISM: Artificial Sequence
<220> FEATURE:
<223> OTHER INFORMATION: Artificially synthesized primer sequence

<400> SEQUENCE: 1
gaagatctat ggatcccaac tgctcctg                                28

<210> SEQ ID NO 2
<211> LENGTH: 27
<212> TYPE: DNA
<213> ORGANISM: Artificial Sequence
<220> FEATURE:
<223> OTHER INFORMATION: Artificially synthesized primer sequence

<400> SEQUENCE: 2
ggaattcagg cgcagcagct gcacttg                                 27
```

COMPOSITION FOR TREATING, IMPROVING, OR PREVENTING PAIN

CROSS REFERENCE TO RELATED APPLICATIONS

This application is a National Stage of International Application No. PCT/JP2012/054408 filed Feb. 23, 2012, claiming priority based on Japanese Patent Application No. 2011-036855 filed Feb. 23, 2011, the contents of all of which are incorporated herein by reference in their entirety.

TECHNICAL FIELD

The present invention relates to a composition and a method for treating, improving, or preventing pain. Moreover, the present invention relates to a method for determining effectiveness of the composition in treating, improving, or preventing pain. Furthermore, the present invention relates to a composition and a method for diagnosing pain.

BACKGROUND ART

Complex regional pain syndrome (CRPS) is a syndrome, in which after a trauma such as a bone fracture or a nerve injury, pain continues with severity disproportionate to the degree of the trauma and lasts persistently. CRPS has been called various names. It is said that CRPS was originally coined by Mitchell in 1867, who described, as causalgia, burning pains after nerve injuries following bullet wounds or the like during the American Civil War. Since then, CRPS has also been called by various names such as algodystrophy, chronic traumaric edema, and painful post-traumatic osteoporosis. Then, it was proposed that stubborn burning pain and abnormal contraction and expansion of blood vessels after a trauma be originated from the sympathetic nervous system. In 1946, Evans introduced such a notion as reflex sympathetic dystrophy (RSD). After that, names such as causalgia and RSD were generally used in pain-related fields. In 1986, the International Association for the Study of Pain clearly defined RSD as one not following an obvious nerve injury, while causalgia as one following a nerve injury. Nevertheless, various controversies arose: among RSD conditions, there is a case not responding to sympathetic blocks or the like; the primary site of the disease is not clear; and so forth. In 1994, Task Force on Taxonomy of the International Association for the Study of Pain unified and defined RSD as CRPS type I and causalgia as CRPS type II up to now.

CRPS is characterized by various symptoms such as allodynia, hyperalgesia, decreased sensation, abnormal tactile sensation, change in skin color, abnormal sweating, skin contraction and pigmentation, wrinkle disappearance and glossing, nail deformation and thinning, limited range of joint movement, bone contraction, weakened muscle strength, and involuntary movement. The most distinctive feature of CRPS is the strength of the pain. The strong and persistent pain disproportionate to the degree of trauma greatly reduces the QOL of the patients. Nonetheless, the medical places where CRPS is treated are full of confusion. The main reason is that the disease has not been elucidated yet. As the conservative treatment method, various treatment methods have been attempted so far, which include: drug therapies (NSAIDS, steroids, strong and weak opioids, antianxiety drugs, anticonvulsant drugs, and the like), physical therapies (training for moving a joint in a range, muscle training, and the like), block therapies (sympathetic blocks, electrical spinal cord stimulation therapy, and the like), and surgical therapies such as neurolysis, neurectomy, and nerve grafting. However, effective treatment methods, particularly effective pharmaceutical compositions, have not been available yet until now.

Meanwhile, metallothionein (MT) is a protein having attracted attention in the central nervous system recently. The increase of this protein has been observed after brain injury and various neurodegenerative diseases such as Alzheimer's disease, Parkinson's disease, and ALS. Further, MT is known to be a protein contributing neuroregeneration (NPLs 1 to 7).

Nevertheless, there have been very little findings about MT in the peripheral nervous system. There has been no report at all regarding a relation between MT and pain of CRPS or the like.

CITATION LIST

Non Patent Literatures

[NPL 1] Chung, R. S. et al., J Biol Chem, 2008, vol. 283, no. 22, pp. 15349 to 58

[NPL 2] Chung, R. S. et al., "The native copper- and zinc-binding protein metallothionein blocks copper-mediated Abeta aggregation and toxicity in rat cortical neurons.", PLoS One, Aug. 11, 2010, vol. 5, issue 8, e12030

[NPL 3] Nagano, S. et al., Eur J Neurosci, 2001, vol. 13, issue 7, pp. 1363 to 70

[NPL 4] Pedersen, M. O. et al., Biofactors, 2009, vol. 35, issue 4, pp. 315 to 25

[NPL 5] Ebadi, M. et al., Exp Biol Med (Maywood), 200 6, vol. 231, no. 9, pp. 1576 to 83

[NPL 6] Chung, R. S. et al., J Neurosci, 2003, vol. 23, no. 8, pp. 3336 to 42

[NPL 7] Stankovic, R. K et al., Neurosci Lett, 2006, vol. 402, issues 1-2, pp. 1 to 6

SUMMARY OF INVENTION

Technical Problems

The present invention has been made in consideration of the above-described problems in the conventional techniques. An object of the present invention is to identify a molecule involved in a pain production mechanism, and to provide a composition and a method for treating, improving, or preventing pain by utilizing the molecule. Another object of the present invention is to provide a method for determining effectiveness of the composition in treating, improving, or preventing pain, by targeting the molecule. Still another object of the present invention is to provide a composition and a method for diagnosing pain by targeting the molecule.

Solution to Problems

The present inventors have earnestly studied in order to achieve the above objects. As a result, the inventors have found out that a metallothionein (MT) protein is expressed in a normal peripheral nerve, and that the expression is not observed in a peripheral nerve producing pain. Further, it has been found out that administering a metallothionein protein to rats having neuropathic pain (neurogenic pain) suppresses the pain in the rats. From these facts, the present inventors have found out that: pain can be, for example, treated by utilizing a metallothionein protein; the effectiveness of, for example, the treatment can be determined on the basis of an expression of the metallothionein protein; and furthermore pain can be diagnosed on the basis of an expression of a metallothionein protein. These discoveries have led to completion of the present invention.

More specifically, the present invention provides the following inventions.

(1) A composition for treating, improving, or preventing pain, the composition comprising any one of a metallothionein protein, a gene encoding the protein, and a vector in which the gene is inserted.

(2) A method for treating, improving, or preventing pain, the method comprising administering any one of a metallothionein protein, a gene encoding the protein, and a vector in which the gene is inserted.

(3) A method for determining effectiveness of the composition according to (1) in treating, improving, or preventing pain of a subject, the method comprising:

detecting an expression of the metallothionein protein in a sample isolated from the subject; and when the expression is significantly lower than an expression of a metallothionein protein in a healthy subject, determining that the composition according to (1) is highly effective in treating, improving, or preventing pain of the subject.

(4) A composition for diagnosing pain, the composition comprising a molecule capable of detecting an expression of a metallothionein protein.

(5) A method for diagnosing pain, the method comprising:

detecting an expression of a metallothionein protein in a sample isolated from a subject; and when the expression is significantly lower than an expression of a metallothionein protein in a healthy subject, determining that the subject has pain or has a risk of developing pain.

Advantageous Effects of Invention

The present invention has revealed that a reduction in an expression of a MT protein is involved in pain production, and that administering a MT protein demonstrates a significant effect in preventing, improving, or treating pain. The present invention makes it possible to treat, improve, or prevent pain on the basis of a novel action mechanism, and to diagnose pain objectively with a novel indicator.

BRIEF DESCRIPTION OF DRAWINGS

The patent or application file contains at least one drawing executed in color. Copies of this patent or patent application publication with color drawing(s) will be provided by the Office upon request and payment of the necessary fee.

DESCRIPTION OF EMBODIMENTS

Composition and Method for Treating, Improving, or Preventing Pain

The present invention provides a composition for treating, improving, or preventing pain, the composition comprising any one of a metallothionein protein, a gene encoding the protein, and a vector in which the gene is inserted. Moreover, the present invention provides a method for treating, improving, or preventing pain, the method comprising administering any one of a metallothionein protein, a gene encoding the protein, and a vector in which the gene is inserted.

In the present invention, a "metallothionein protein" is a protein rich in cysteine residues and having a high affinity for heavy metals (hereinafter, metallothionein may also be referred to as "MT"). An organism from which a metallothionein protein is derived is not particularly limited. Examples thereof include human, pig, cattle, horse, sheep, goat, chicken, duck, ostriches, domesticated duck, dog, cat, rabbit, hamster, mouse, rat, monkey, and the like. When used to treat or prevent pain of a human, the metallothionein protein is preferably derived from human. Examples of the human-derived MT protein include MT-1A, MT-1B, MT-1E, MT-1F, MT-1G, MT-1H, MT-1M, MT-1X, MT-2A, MT-3, and MT-4. Typically, human MT-1A is a protein (gene) specified by ACCESSION No. NP_005937 (NM_005946); human MT-1B is a protein (gene) specified by ACCESSION No. NP_005938 (NM_005947); human MT-1E is a protein (gene) specified by ACCESSION No. NP_783316 (NM_175617); human MT-1F is a protein (gene) specified by ACCESSION No. NP_005940 (NM_005949); human MT-1G is a protein (gene) specified by ACCESSION No. NP_005941 (NM_005950); human MT-1H is a protein (gene) specified by ACCESSION No. NP_005942 (NM_005951); human MT-1M is a protein (gene) specified by ACCESSION No. NP_789846 (NM_176870); human MT-1X is a protein (gene) specified by ACCESSION No. NP_005943 (NM_005952); human MT-2A is a protein (gene) specified by ACCESSION No. NP_005944 (NM_005953); human MT-3 is a protein (gene) specified by ACCESSION No. NP_005945 (NM_005954); and human MT-4 is a protein (gene) specified by ACCESSION No. NP_116324 (NM_032935).

Moreover, in the present invention, the "metallothionein protein" includes mutants whose amino acid sequences are mutated in comparison with the wild type MT proteins by amino acid substitution, deletion, addition, insertion, or the like, as long as the mutants have an equivalent function to those of the wild type MT proteins. The mutation may be induced naturally (i.e., non-artificially), or may be introduced artificially. A mutation may be artificially introduced by, for example, site-directed mutagenesis (Kramer, W. & Fritz, H J., Methods Enzymol, 1987, 154, 350.). In such a mutant, the number of amino acids mutated is not particularly limited, as long as the function thereof is retained. The number is normally 10 amino acids or less, preferably 5 amino acids or less (for example, 3 amino acids or less, 2 amino acids or less, or 1 amino acid).

Further, in the present invention, the "metallothionein protein" includes proteins encoded by DNAs having a high homology with DNAs encoding the wild type MT proteins, as long as such proteins have an equivalent function to those of the wild type MT proteins. Here, the "high homology" refers to a sequence homology at a base level of at least 70% or more, preferably 80% or more, and further preferably 90% or more (for example, 95% or more). The homology of amino acid sequences and base sequences can be determined with an algorithm BLAST developed by Altschul et al. (J. Mol. Biol. 215, 403-410 (1990); Nucl. Acids Res. 17, 3389-3402 (1997)). The parameters are set at, for example, E value=0.01, while the default values are used for the others. The specific procedures of these analysis methods are known (http://www.ncbi.nlm.nih.gov/.).

Those skilled in the art can prepare a DNA encoding such a protein by utilizing known hybridization techniques (for example, the method described in Hanahan, D. et al., Meth. Enzymol., 1983, vol. 100, pp. 333 to 342, and the method described in Benton, W. D. et al., Science, 1977, pp. 180 to 182). Specifically, those skilled in the art can carryout hybridization by utilizing the DNAs encoding the wild type MT proteins or portions of the DNAs, isolate DNAs having a high homology therewith from various other organisms, and further obtain proteins having an equivalent function to those of the wild type MT proteins from the DNAs thus isolated. As stringent conditions for the hybridization to isolate the DNAs having a high homology with the DNAs encoding the wild type MT proteins, it is possible to employ conditions for carrying out the hybridization with "6×SSC and 40% formamide at 25° C." and washing with "1×SSC at 55° C.". As more preferable conditions, it is possible to employ conditions for carrying out the hybridization with "6×SSC and 40% formamide at 37° C." and washing with "0.2×SSC at 55° C.". As further preferable conditions, it is possible to employ the hybridization with "6×SSC and 50% formamide at 37° C." and washing with "0.1×SSC at 62° C.". It should be noted that those skilled in the art can set up stringent hybridization conditions equivalent to the conditions described above by appropriately selecting conditions such as the dilution ratio of SSC, the formamide concentration, and the temperature.

Moreover, the DNAs having a high homology with the DNAs encoding the wild type MT proteins can also be prepared by utilizing gene amplification techniques such as polymerase chain reaction (PCR).

Further, the "metallothionein protein" according to the present invention includes partial peptides thereof, as long as having an equivalent function to those of the wild type MT proteins. Such partial polypeptides are polypeptides having a length of at least 10 amino acids, preferably 15 amino acids, and further preferably 20 amino acids or more.

The phrase that the prepared proteins (including mutants thereof) and partial peptides "have an equivalent function to" those of the wild type MT proteins means these have an effect of preventing or treating pain. Whether the proteins and the like have the effect or not can be determined by a pain-related behavior evaluation using a Seltzer model or the like as described later in Examples.

The MT protein according to the present invention can be prepared by selecting known methods as appropriate. The naturally-occurring proteins can be prepared, for example, by a method in which a liquid extract of a kidney or liver tissue having the wild type MT proteins expressed at a high level is subjected to affinity chromatography using an anti-MT protein antibody. Meanwhile, the recombinant protein can be prepared, for example, by inserting a DNA encoding the MT protein according to the present invention into an appropriate expression vector, culturing a transformant obtained by introducing the vector into appropriate cells, and purifying a protein expressed thereby.

More specifically, in a case where the host is *Escherichia coli*, a plasmid vector pET-3 (Rosenberg, A. H. et al., Gene 56, 125-35 (1987)), pGEX-1 (Smith, D. B. and Johnson, K. S., Gene 67, 31-40 (1988)), or the like is used. The *Escherichia coli* transformation can be carried out by a heat shock method (for example, calcium chloride method, Hanahan method, Inoue method, rubidium chloride method), an electroporation method, or the like. In a case where the host is a fission yeast (*Schizosaccharomyces pombe*), a plasmid vector pESP-1 (Lu, Q. et al., Gene 200, 135-144 (1997)) or the like is used. The yeast transformation can be carried out, for example, by a spheroplast method, a lithium acetate method, an electroporation method, or the like. In a case where the host is insect cells, a baculovirus vector pBacPAK8/9 (BD Clontech) or the like is used. The insect cell transformation can be carried out, for example, according to the method described in Bio/Technology, 6, 47-55 (1980)) or the like. Additionally, in a case where the host is mammalian cells, for example, CHO cells, HeLa cells, or the like, a vector such as pMSG (BD Clontech) is used. The recombinant DNA is introduced into mammalian cells by a phosphate calcium method (Graham, F. L. and van der Eb, A. J., Virology 52, 456-467 (1973)), a DEAE-dextran method (Sussman, D. J. and Milman, G., Mol. Cell. Biol. 4, 1641-1643 (1984)), a lipofection method (Felgner, P. L. et al., Proc. Natl. Acad. Sci. USA 84, 7413-7417 (1987)), an electroporation method (Neumann, E. et al., EMBO J. 1, 841-845 (1982)), or the like. Moreover, the recombinant protein expressed in the host cells can be purified by known methods. For example, the recombinant protein can be synthesized in the form of a fusion protein with a histidine residue tag, a glutathione S-transferase (GST), or the like attached at the N-terminus of the protein, and then purified through binding to a metal-chelating resin or a GST affinity resin (Smith, M. C. et al., J. Biol. Chem. 263, 7211-7215 (1988)). Further, when pESP-1 is used as the vector, the protein of interest is synthesized as a fusion protein with the glutathione S-transferase (GST); hence, the recombinant protein can be purified through binding to a GST affinity resin. In order to separate the protein of interest from the fusion protein, for example, thrombin, blood coagulating factor Xa, or the like is used for prescission. Nonetheless, as described later in Examples, even if the fusion protein is attached to the MT protein, the MT protein has an effect of preventing or treating pain. For this reason, the treatment such as prescission is not necessary for the MT protein according to the present invention, and the MT protein to which the fusion protein obtained easily at a relatively low cost is attached can also be suitably used.

Typical examples of the "gene encoding the metallothionein protein" according to the present invention include the genes specified by ACCESSION Nos. mentioned above. Moreover, the "vector in which the gene encoding the metallothionein protein is inserted" according to the present invention should be capable of expressing the inserted "gene encoding the metallothionein protein" in animal cells. Examples of the vector capable of expressing the "gene encoding the metallothionein protein" include plasmid DNAs such as pMSG (BD Clontech), viral vectors such as retroviral vectors (Danos, O. and Mulligan, R. C., Proc. Natl. Acad. Sci. USA 85, 6460-6464 (1988); Dranoff, et al., Proc. Natl. Acad. Sci. USA 90, 3539-3543 (1993)), and adenoviral vectors (Wickham, T. J. et al., Cell 73, 309-319 (1993)), and the like, but the examples are not limited thereto.

In the present invention, "pain" means the result of the following events: a physical stimulus or a chemical stimulus from an algesic substance (serotonin, bradykinin, or the like) is sensed by a pain nerve terminal, and the stimulus is converted into an electrical signal, then passes through the lateral spinothalamic tract that is an afferent path for pain and temperature perceptions, and is recognized as pain by the postcentral gyrus of the cerebrum. In the present invention, pain is not particularly limited. An example thereof includes pain produced by entrapment neuropathy, refractory pain, or spine diseases.

Examples of entrapment neuropathy include carpal tunnel syndrome, cubital tunnel syndrome, Guyon's canal syndrome, thoracic outlet syndrome, tarsal tunnel syndrome, and Morton disease. Examples of refractory pain include so-called neuropathic pain (neurogenic pain) such as CRPS, diabetic neuropathy, arm nerve injury, intercostal neuralgia (postherpetic neuralgia), carcinomatous neuropathy, painful neuromas, phantom pain, and post-surgery pain syndrome. Note that "neuropathic pain" means pain caused by a primary injury to nerve systems or an abnormal function thereof, the pain produced by various causes such as neuropathy by a neurotoxic substance, chemotherapy, or the like, peripheral nerve injuries by trauma, phantom pain by amputation, radiculopathy by disc herniation, metabolic diseases, infections, tumor invasions, spinal cord injuries, stroke, and multiple sclerosis. In addition, examples of spine diseases include cervical/lumber disc herniation, spinal cord injury, and spinal canal stenosis.

All of these diseases are accompanied by pain caused by a physical or chemical damage to a peripheral nerve. Hence, as apparent from the fact as shown in Table 4 described later that a MT protein disappeared in painful neuromas (one had amputation neuroma as a result of a dismemberment, and another had a neuroma caused after wrist cutting), a MT protein disappears or decreases in such peripheral nerve disorders (damages). Moreover, as described in Examples 3 and 4 later, administering a MT protein to these damaged peripheral nerves relieves the pain. Thus, the composition of the present invention can be suitably used for treating, improving, or preventing pain in these diseases, can be more suitably used for treating, improving, or preventing pain in neuropathic pain, and can be particularly suitably used for treating, improving, or preventing pain of CRPS.

The composition of the present invention may be in a form of a pharmaceutical composition, a food or drink (including an animal feed), or a reagent used for a research purpose (for example, in vitro or in vivo experiment).

Since having an action of relieving pain, the composition of the present invention can be suitably used as a pharmaceutical composition to be administered for treating or preventing pain, for example, pain caused by entrapment neuropathy, refractory pain, and spine diseases mentioned above, or other pains, or as a food or drink routinely taken for improving or preventing pain.

The composition of the present invention can be formulated by known formulation methods. The composition of the present invention can be used orally or parenterally in the form of, for example, a capsule, a tablet, a pill, a liquid, a powder, a granule, a fine granule, a film coating agent, a pellet, a troche, a sublingual tablet, a masticatory, a buccal, a paste, a syrup, a suspension, an elixir, an emulsion, a topical agent, an ointment, a plaster, a poultice, a percutaneous absorption preparation, a lot ion, an inhalation, an aerosol, an injection, a suppository, or the like.

When formulated, these can be combined as appropriate with a pharmacologically acceptable carrier or medium, specifically, for example, sterile water, a saline, a vegetable oil, a solvent, a base, an emulsifier, a suspension, a surfactant, a stabilizer, a flavor, an aromatic, an excipient, a vehicle, an antiseptic, a binder, a diluent, an isotonic agent, a soothing agent, a filler, a disintegrator, a buffer, a coating agent, a lubricant, a colorant, a sweetener, a viscous agent, a flavoring agent, a solubilizer, or other additives. Moreover, when used as a pharmaceutical composition, the composition of the present invention may be used in combination with a known pharmaceutical composition used for treating or preventing the aforementioned diseases such as entrapment neuropathy, refractory pain, or spine diseases.

The method for administering the pharmaceutical composition of the present invention is not particularly limited. Examples thereof include oral administration, intravenous administration, intraarterial administration, intraperitoneal administration, subcutaneous administration, intradermal administration, intraneural administration, tracheobronchial administration, intrarectal administration, intramuscular administration, and administration by transfusion. Moreover, examples of a preferable method for administering the pharmaceutical composition of the present invention include direct injection into a peripheral nerve producing pain, injection into skin near a peripheral nerve producing pain, transdermal administration with a percutaneous absorption preparation or the like, and intraperitoneal administration. An example of a more preferable administration method is intraperitoneal administration.

When the composition of the present invention is used as a food or drink, the food or drink may be, for example, a health food, a functional food, a food for specified health food, a nutritional supplementary food, a medical food for the ill, a food additive, or an animal feed. The food or drink of the present invention can be taken as the composition as described above, or can also be taken as various foods or drinks. Specific examples of the foods or drinks include oil-containing products such as vegetable oils, dressings, mayonnaise, and margarines; liquid foods such as soups, milk drinks, soft drinks, tea drinks, alcoholic drinks, energy drinks, jelly drinks, functional drinks; carbohydrate-containing foods such as cereals, noodles, and breads; livestock-processed foods such as hams and sausages; processed seafoods such as kamaboko, stockfishes, and shiokara; vegetable-processed foods such as tsukemono; semi-solid foods such as jellies and yogurts; fermentation foods such as miso and fermented drinks; various confectionaries such as Western style confections, Japanese-style confections, candies, gums, gummies, frozen desserts, and frozen confections; retort pouch foods such as curries, thick starchy sauces, and Chinese soups; convenience foods and microwave foods such as convenience soups and convenience miso soup; and the like. The examples further include health foods or drinks prepared into a powder, a granule, a tablet, a capsule, a liquid, a paste or a jelly. The composition of the present invention can be used targeting animals including human. The animals other than human are not particularly limited, a variety of livestock, poultry, pets, experimental animals, and the like can be targeted. Specific examples thereof include pigs, cattle, horses, sheep, goats, chickens, ducks, ostriches, domesticated ducks, dogs, cats, rabbits, hamsters, mice, rats, monkeys, and the like, but the examples are not limited thereto.

In the present invention, the food or drink can be produced by production techniques known in this technical field. To the food or drink, an ingredient or two or more ingredients effective in improving or preventing the disease such as entrapment neuropathy, refractory pain, and spine diseases may be added. Moreover, in combination with another ingredient or another functional food, which demonstrate a function other than relieving pain, a multifunctional food or drink can be provided.

When the composition of the present invention is administered or taken, the amount administered or the amount taken is selected as appropriate in accordance with the age, weight, symptom, and health state of the target, the type of the composition (such as drug, food, or drink), and so forth. For example, the amount of the pharmaceutical composition of the present invention administered at one time is preferably 800 ng/kg body weight to 8 mg/kg body weight based on the active ingredient protein. When the composition is administered as the gene, the composition is preferably administered in such a manner that the protein is expressed within the aforementioned range of the administration amount.

In this manner, the present invention makes it possible to treat, improve, or prevent pain by, for example, administration or ingestion by the target of the composition of the present invention. Thus, the present invention also provides the method for treating, improving, or preventing pain, the method comprising administering any one of a metallothionein protein, a gene encoding the protein, and a vector in which the gene is inserted.

A product (drug, food, drink, reagent) of the composition of the present invention or a protocol thereof may be a labelled to indicate that the use is to treat, improve, or prevent pain. Herein, the phrase "a product or a protocol is labeled" means that the body of the product, a container or a package therefor, or the like is labeled, or that a protocol, an attachment document, advertisement, other prints, or the like disclosing information on the product is labeled.

Note that, as an embodiment of the present invention, possibly a molecule capable of promoting an expression of the metallothionein protein is also administered to treat, improve, or prevent pain. Thus, the present invention can provide a composition for treating, improving, or preventing pain, the composition comprising a molecule capable of promoting an expression of the metallothionein protein. Further, the present invention can also provide a method for treating, improving, or preventing pain, the method comprising promoting an expression of the metallothionein protein.

In the embodiment, the "promotion of the expression of the metallothionein protein" may be achieved by any of a promotion at a transcription stage and a promotion at a translation stage, as long as the expression of the metallothionein protein is promoted in the end. Examples of the "molecule capable of promoting an expression of the metallothionein protein" include metals such as cadmium, bismuth, and copper, and metal salts thereof, which are known to induce a synthesis of the metallothionein protein (see Min et al., the Journal of Therapy, July, 2006, vol. 88, no. 7, pp. 1853 to 1858). Moreover, the example also includes pergolide mesylate because it has been reported that administering pergolide mesylate to Parkinson's disease model rats increases the concentration of metallothionein mRNA in the striata (see Ono et al., Biol. Pharm. Bull., 2009, vol. 32, pp. 1813 to 1817). Furthermore, an example of the method for "promoting an expression of the metallothionein protein" according to the present invention includes a physical therapy because it is known that a physical therapy increase the concentration of metallothionein mRNA in the brain of an ALS patient.

<Method for Determining Effectiveness of the Composition of the Present Invention in Treating, Improving, or Preventing Pain>

The present invention provides a method for determining effectiveness of the composition in treating, improving, or preventing pain of a subject, the method comprising:

detecting an expression of the metallothionein protein in a sample isolated from the subject; and when the expression is significantly lower than an expression of a metallothionein protein in a healthy subject, determining that the composition of the present invention is highly effective in treating, improving, or preventing pain of the subject.

In the present invention, the "subject" is not particularly limited. Examples thereof include a human, a pig, a cattle, a horse, a sheep, a goat, a chicken, a duck, an ostrich, a domesticated duck, a dog, a cat, a rabbit, a hamster, a mouse, a rat, a monkey, and the like. Moreover, the subject does not necessarily have to have pain (for example, the pain produced by entrapment neuropathy, refractory pain, or spine diseases).

In the present invention, a "sample isolated from a subject" should be a cell, a tissue, a body fluid, or the like, and in a corresponding sample of a healthy subject, an expression of a metallothionein protein is observed. Examples thereof include blood, peripheral nerve, skin, and mucous membrane. Moreover, the method for isolating the sample is not particularly limited, and known methods suitable for the target cell, tissue, body fluid, or the like can be employed as appropriate. Note that, in the present invention, a "healthy subject" means one not having pain (for example, the pain produced by entrapment neuropathy, refractory pain, or spine diseases).

In the present invention, the "expression of the metallothionein protein" means to include both transcription and translation of the gene encoding the metallothionein protein. Thus, in the present invention, the "detecting an expression of a protein" includes not only detecting the metallothionein protein, but also detecting metallothionein mRNA. Note that the method for isolating the sample of the metallothionein protein or the metallothionein mRNA is not particularly limited, and known methods suitable for the target cell, tissue, body fluid, or the like can be employed as appropriate.

In the present invention, known methods can be employed for "detecting an expression of the metallothionein protein." Examples of the method for detecting the metallothionein protein include detection methods using an antibody capable of binding to a metallothionein protein (immunological method) such as immunohistochemical staining, imaging cytometry, flow cytometry, ELISA, radioimmunoassay, immunoprecipitation, immunoblotting, and antibody array. Moreover, examples of the method for detecting an mRNA encoding a metallothionein protein include RT-PCR, DNA microarray analysis, northern blotting, in situ hybridization, dot blot, and RNase protection assay.

As a result of detecting the expression of the metallothionein protein in the sample isolated from the subject, when the expression is significantly lower than an expression of a metallothionein protein in a healthy subject, it is determined that the composition of the present invention is highly effective in treating, improving, or preventing pain of the subject. In contrast, when the expression is equivalent to the expression of a metallothionein protein in a healthy subject, it is determined that the composition of the present invention is not highly effective in treating, improving, or preventing pain of the subject.

<Composition and Method for Diagnosing Pain>

The present invention provides a composition for diagnosing pain, the composition comprising a molecule capable of detecting an expression of a metallothionein protein. In addition, the present invention provides a method for diagnosing pain, the method comprising:

detecting an expression of a metallothionein protein in a sample isolated from a subject; and when the expression is significantly lower than an expression of a metallothionein protein in a healthy subject, determining that the subject has pain or has a risk of developing pain.

In the present invention, the "molecule capable of detecting an expression of a metallothionein protein" is not particularly limited, as long as the detection is possible. An example thereof includes molecules used in the aforementioned methods exemplified for "detecting an expression of the metallothionein protein". Specific examples thereof include an antibody capable of binding to a metallothionein protein, and a polynucleotide (such as polynucleotide primer, polynucleotide probe) specifically hybridizing to an mRNA encoding a metallothionein protein. The polynucleotide normally has a length of at least 15 bases complementary to the base sequence of the mRNA encoding a metallothionein protein. Herein, being "complementary" does not always have to mean that all the base sequences (i.e., completely) are complementary to each other, as long as the detection is possible. Such an antibody and a polynucleotide may be labeled as necessary. The methods for preparing and labeling the antibody and polynucleotide are known to those skilled in the art.

The composition may comprise other ingredients in addition to the molecule capable of detecting an expression of a metallothionein protein. Examples of the other ingredients include a carrier, an excipient, a disintegrator, a buffer, an emulsifier, a suspension, a stabilizer, a preservative, an antiseptic, a physiological salt, a labeled compound, a secondary antibody, and the like. As the excipient, lactose, starch, sorbitol, D-mannitol, white sugar, or the like can be used. As the disintegrator, starch, carboxymethyl cellulose, calcium carbonate, or the like can be used. As the buffer, a phosphate, a citrate, an acetate, or the like can be used. As the emulsifier, gum arabic, sodium alginate, tragacanth, or the like can be used. As the suspension, glyceryl monostearate, aluminium monostearate, methyl cellulose, carboxymethyl cellulose, hydroxymethyl cellulose, sodium lauryl sulfate, or the like can be used. As the stabilizer, propylene glycol, diethylin sulfite, ascorbic acid, or the like can be used. As the preservative, phenol, benzalkonium chloride, benzyl alcohol, chlorobutanol, methylparaben, or the like can be used. As the antiseptic, benzalkonium chloride, para-hydroxybenzoic acid, chlorobutanol, or the like can be used.

A kit can also be provided by combining the composition with other preparations necessary for a diagnosis. Examples of the other preparations include a substrate necessary for detection of a label, a positive control or a negative control, a buffer solution used to dilute or wash a sample, and the like. Moreover, in a case where the preparation is an unlabeled antibody, the kit may comprise a labeled substance (for example, a secondary antibody, Protein G, Protein A, or the like) capable of binding to the antibody. Further, the kit may comprise an instruction.

EXAMPLES

Hereinafter, the present invention will be described more specifically based on Examples. However, the present invention is not limited to the following Examples.

Example 1

Proteomic Analysis on Peripheral Nerves of CRPS Patients

Proteins were extracted from three specimens of peripheral nerves of CRPS patients ("CRPS1 to 3" described in Table 1), and from two specimens of sural nerves excised from fresh cadavers as controls (normal nerves) ("controls 1 and 2" described in Table 1). Both of which were stored at −80° C. after the excision. See Table 1 for details of the nerves used. Specifically, 5 mm of each nerve specimen was homogenized in 200 μL of an extraction buffer (40 mM Tris base, 0.5% Triton X-100, 10% glycerol, 5 mM EDTA, 2 mM Pefabloc), then shaken at 4° C. for 30 minutes, and further ultracentrifuged at 100,000 G at 4° C. for 30 minutes to separate the soluble fraction and the insoluble fraction from each other. To the obtained insoluble fraction, 100 μL of 1% SDS was further added. After heating at 70° C. for 30 minutes, the resultant was ultracentrifuged at 40000 g at 22° C. for 30 minutes to extract the supernatant. The soluble fraction was treated with TCA, precipitated, and thereafter dissolved into SDS-U (0.2 M Tris-HCl, 4% SDS, 8 M urea, 0.1% DTT, 0.01% bromophenol blue). Moreover, the supernatant of the insoluble fraction was also dissolved into SDS-U. Note that the peripheral nerves of the CRPS patients was obtained with the consent of the patients when the neurectomy was performed as a treatment, and the normal nerves were obtained from bodies donated to Sapporo Medical University.

A peptide analysis was conducted on the obtained protein liquid extract by employing a proteomic method with a mass spectrometer. Specifically, first, 200 μg of each protein of the soluble fraction and the insoluble fraction was set on a 8 to 20% polyacrylamide gel, and allowed to migrate to approximately 10 cm (at 10 V, overnight) for fractionation. Then, this polyacrylamide gel was stained with silver using Ez Stain Silver Kit (manufactured by Atto Corporation), and subsequently immersed in a fixing solution (100 mL of methanol, 80 mL of ultrapure water (for example, Milli-Q water. The same shall apply hereinafter), 20 mL of acetic acid, 2 mL of S-1 solution) followed by shaking for 10 minutes. Then, after the fixing solution was discharged, the resultant was immersed in ultrapure water and shaken for 10 minutes. The polyacrylamide gel was washed, and further the ultrapure water was discharged. After this washing operation was repeated three times, the polyacrylamide gel was immersed in a staining solution (200 mL of ultrapure water, 2 mL of S-2 solution) and shaken for 5 minutes. Thereafter, the staining solution was discharged. Subsequently, the polyacrylamide gel was immersed in ultrapure water, and shaken for 30 seconds precisely. Then, the liquid was discharged. Thereafter, the polyacrylamide gel was immersed in a half of a coloring solution (400 mL of ultrapure water, 2 mL of S-3 solution, 2 mL of S-4 solution), and shaken for 30 seconds precisely. Then, the liquid was discharged. Furthermore, the resultant was immersed in the other half of the coloring solution and shaken until appropriately colored, and the liquid was discharged. Then, after the polyacrylamide gel was immersed in a stop solution (500 mL of ultrapure water, 5 mL of acetic acid), and shaken for 10 minutes, the bands (the proteins of the soluble fraction and the insoluble fraction thus fractionated) were checked by OHP scanning.

Next, in order to identify the bands checked by the OHP scanning, the polyacrylamide gel stained with silver as described above was subjected to reduction and alkylation treatment and further subjected to trypsin treatment. Specifically, the polyacrylamide gel was immersed in 50 mM Tris (pH 8.8) and shaken for 1 minute. Then, the liquid was discharged. Further, the resultant was immersed in a 10 mM DTT solution (the solution was obtained by dissolving 0.5 g of a DTT powder in 50 ml of 50 mM Tris (pH 8.8)) and shaken for 15 minutes, and then the liquid was discharged. Subsequently, the polyacrylamide gel was immersed in an IAA solution (the solution was obtained by dissolved 1 g of Iodoacetoamide powder in 50 ml of 50 mM Tris (pH 8.8)) and shaken for 15 minutes. Then, the liquid was discharged. Thereafter, the polyacrylamide gel was immersed in a stop solution (1% acetic acid) and shaken for 10 minutes. After that, the polyacrylamide gel treated as described above was cut into a die-like shape with each side of 1 mm. Then, ACN was added. After the mixture was shaken for 10 minutes, the ACN was removed. Subsequently, the resultant was treated with Speed Vac for 15 minutes, and these gels were dried. Thereafter, 100 mM Ambic was added to the dried gels and shaken for 10 minutes. After that, the Ambic was removed. Then, after ACN was added thereto and shaken for 10 minutes, the ACN was removed. Subsequently, the resultant was treated with Speed Vac for 15 minutes, and these gels were dried. Further, after 100 mM Ambic was added to the dried gels and shaken for 30 minutes, the Ambic was removed. Then, after ACN (750 μl) was added thereto and shaken for minutes, the ACN was removed. Subsequently, the resultant was treated with Speed Vac for 30 minutes, and these gels were dried. A trypsin solution (12.5 ng/μL in 50 mM $NH_4HCO_3$, 5 mM $CaCl_2$) was added to the dried gels thus obtained, and incubated at 37° C. overnight.

Next, peptides were extracted from the gels treated with trypsin as described above, and subjected to mass spectrometry. Specifically, 20 mM Ambic was added to the trypsin-treated gels, and subjected to ultrasonication for 20 minutes. After gentle centrifugation, the liquid was collected. Then, 5% FA/50% ACN was added to the collected liquid, and subjected to ultrasonication for 20 minutes. After gentle centrifugation, the liquid was collected. This collecting operation was repeated three times. Subsequently, the liquid thus collected was centrifuged at 20 KG at 22° C. for 20 minutes. Thereafter, the obtained supernatant was transferred to a fresh Eppendorf tube, and the supernatant was evaporated until the liquid amount became approximately 50 μL. Then, after 15-minute ultrasonication, the resultant was transferred to an ultracentrifugation tube and ultracentrifuged at 40 KG at 22° C. for 30 minutes. The samples obtained as described above were analyzed with 4800 plus MALDI TOF/TOF Analyzer (manufactured by Applied BioSystems Inc.). Using mass spectrometer-dedicated software (protein pilot ver 3.), a database analysis was conducted on MS and MS/MS data obtained from five specimens (three CRPS specimens, two Fresh cadaver specimens) so as to identify the proteins. Table 2 shows that, among the obtained result, no protein expression was observed in the peripheral nerves of the CRPS patients. Note that, in Table 2, "unused (Prot Score)" shows scores calculated from the reliability of the peptides used to identify the proteins.

TABLE 1

|  | Collected Nerve | Age | Gender |
|---|---|---|---|
| CRPS1 | dorsal branch of ulnar nerve | 38 | female |
| CRPS2 | first palmer digital nerve | 47 | male |
| CRPS3 | palmar branch of median nerve | 76 | female |
| Control 1 | sural nerve | 80 | male |
| Control 2 | sural nerve | 88 | female |
| Control 3 | sural nerve | 86 | female |

TABLE 2

| Protein name | ACCESSION No. | Unused (Prot Score) | coverage (%) |
|---|---|---|---|
| Metallothionein 2A | spt\|P02795 | 7.38 | 83.6 |
| Metallothionein-1H | spt\|P80294 | 4 | 34.4 |
| C-reactive protein precursor | spt\|P02741 | 4 | 13.4 |
| OTTHUMP00000030191 | trm\|Q9NTT1 | 2.08 | 12.9 |
| PHYHD1 protein | trm\|Q7Z7P9 | 2 | 4.4 |
| Metallothionein-1G | spt\|P13640 | 0.77 | 67.2 |
| MTE | trm\|Q86YX3 | 0.55 | 34.4 |

The result of the above analysis revealed that no protein was specifically increased in the peripheral nerves of the CRPS patients, and that metallothionein (MT) was one not specifically expressed in the peripheral nerves of the CRPS patients (see Table 2).

Example 2

Analysis of MT Expression in Peripheral Nerve of CRPS Patients

Figure 1:
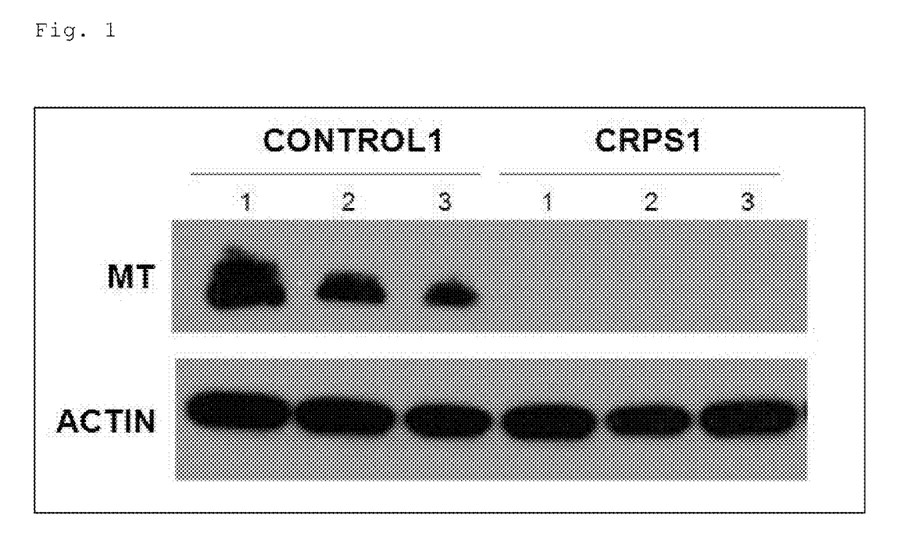
FIG. 1 shows photographs for illustrating the result of examining expressions of a metallothionein protein in peripheral nerves of CRPS patients by western blotting.
Figure 2:
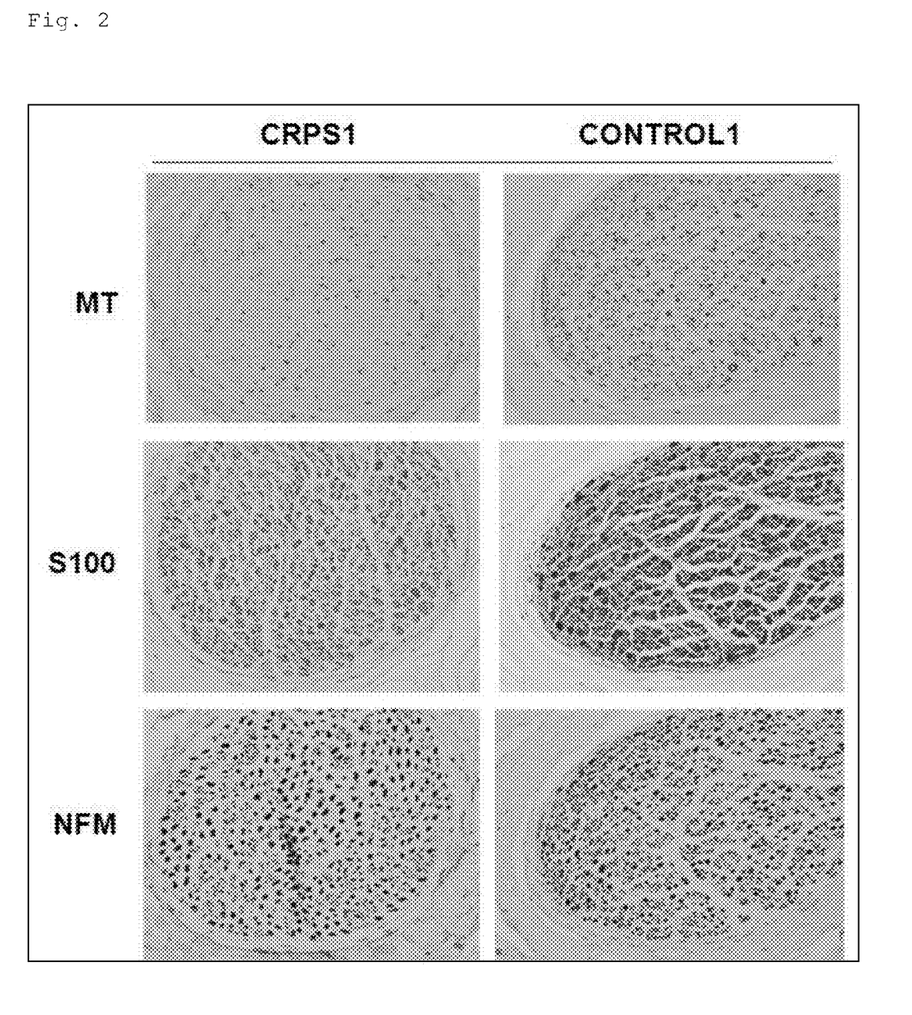
FIG. 2 shows micrographs for illustrating the result of examining metallothionein-protein expression sites in the peripheral nerves of the CRPS patients by immunostaining. Note that, in the figure, "MT" shows the immunostaining result obtained using an anti-metallothionein antibody, "S100" shows the immunostaining result obtained using an antibody against S100 that is a marker specific to Schwann cells, and "NFM" shows the immunostaining result obtained using an antibody against NFM that is a marker specific to an axon.
Figure 3:
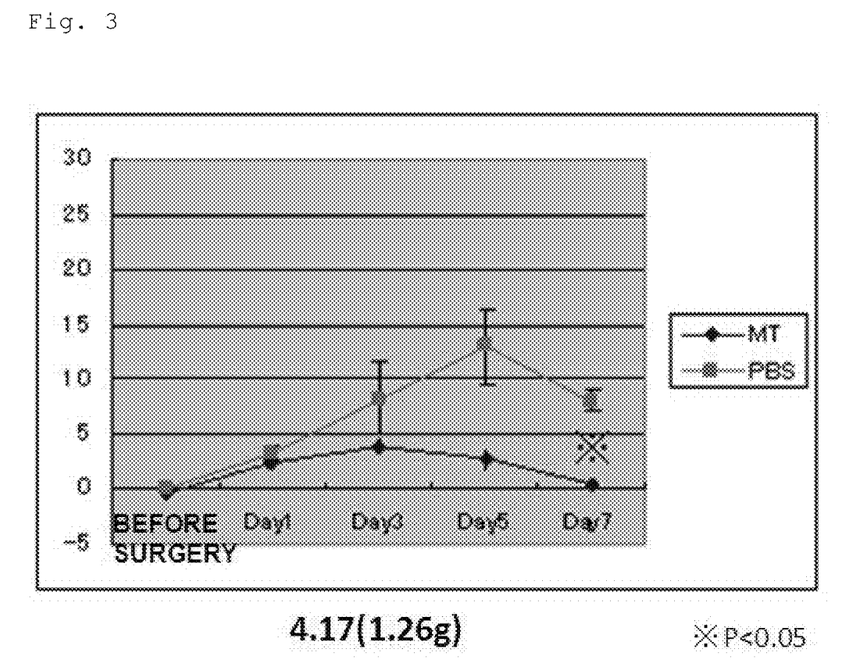
FIG. 3 shows a graph for illustrating the result of examining the effect of locally administering MT on pain of a Seltzer model by a von Frey test (stimulus: 1.26 g). Note that the horizontal axis shows the results on Day 1, Day 3, Day 5, and Day 7 after the day of the surgery for preparing the Seltzer model, and before the surgery. The vertical axis indicates a value obtained as follows: a total number of times of a withdrawal response made to the stimulus to a left (unaffected side) hind paw of the Seltzer model was subtracted from a total number of times of a withdrawal response made to the stimulus to a right (affected side) hind paw.
Figure 4:
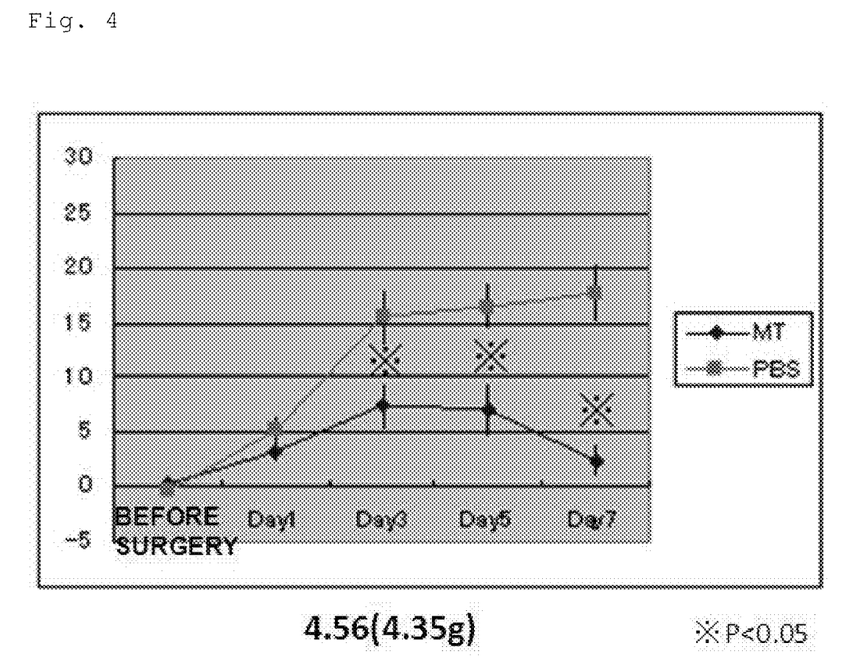
FIG. 4 shows a graph for illustrating the result of examining the effect of locally administering MT on pain of the Seltzer model by a von Frey test (stimulus: 4.35 g). Note that the horizontal axis shows the results on Day 1, Day 3, Day 5, and Day 7 after the day of the surgery for preparing the Seltzer model, and before the surgery. The vertical axis indicates a value obtained as follows: a total number of times of a withdrawal response made to the stimulus to a left (unaffected side) hind paw of the Seltzer model was subtracted from a total number of times by a right (affected side) hind paw.
Figure 5:
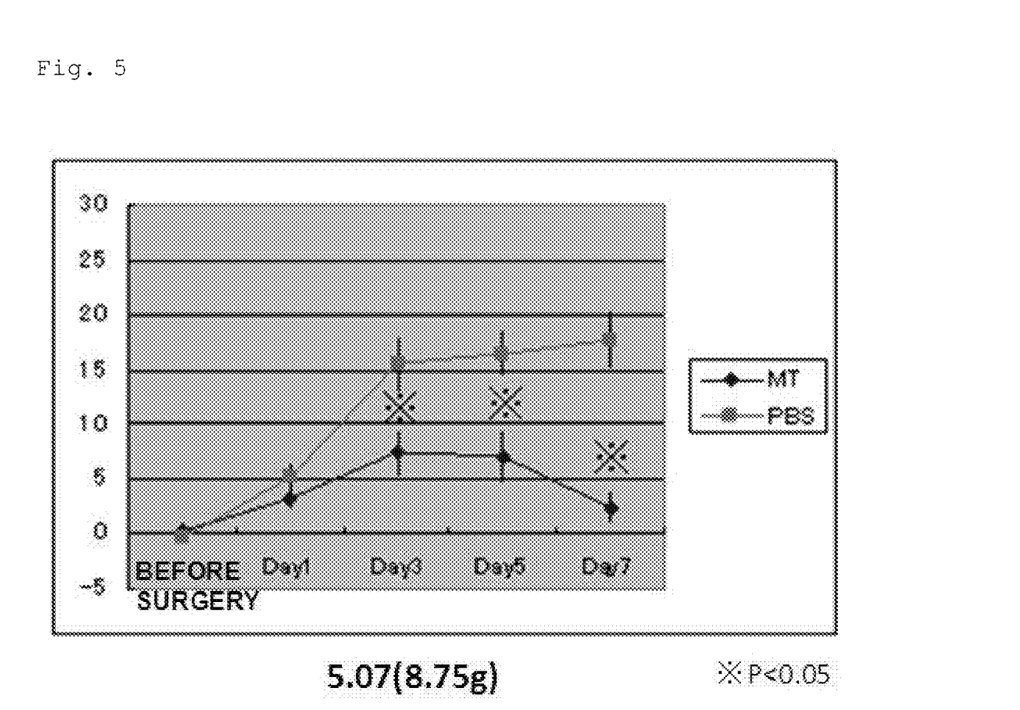
FIG. 5 shows a graph for illustrating the result of examining the effect of locally administering MT on pain of the Seltzer model by a von Frey test (stimulus: 8.75 g). Note that the horizontal axis shows the results on Day 1, Day 3, Day 5, and Day 7 after the day of the surgery for preparing the Seltzer model, and before the surgery. The vertical axis indicates a value obtained as follows: a total number of times of a withdrawal response made to the stimulus to a left (unaffected side) hind paw of the Seltzer model was subtracted from a total number of times by a right (affected side) hind paw.

From the result of the proteomic analysis on peripheral nerves of the CRPS patients, next, the expression and the localization of the MT protein in the peripheral nerves of the CRPS patients were analyzed by western blotting and immunostaining. FIG. 1, FIG. 2, Table 3, and Table 4 show the obtained results. Note that Table 3 shows the staining intensity of each protein (MT, S100, NFM) in each sample (the peripheral nerves of the CRPS patients (CRPS1 to 3) and the normal nerves (controls 1 to 3)). Table 4 shows the result of further immunostaining five CRPS specimens, two painful neuroma specimens, and 57 peripheral nerve specimens included in pathological blocks obtained by wide range excision owing to orthopedic diseases. In other words, Table 4 shows that the expression of the MT protein in each sample (peripheral nerves of the CRPS patients, painful neuroma patients, fresh cadavers, benign tumors, and malignant tumor patients) was either positive or negative by immunostaining. In addition, the methods of western blotting and immunostaining are as described below.

<Western Blotting>

Each sample was fractionated by SDS-PAGE. Specifically, first, 5 mm of a peripheral nerve sample was homogenized in 100 μL of T-PER (registered trademark) Tissue Protein Extraction Reagent, 1 μL of HaltT (registered trademark) protease inhibitor, and 1 μL of 0.5M EDTA (manufactured by Thermo Fisher Scientific Inc.). Subsequently, the resultant was shaken at 4° C. for 30 minutes, and then ultracentrifuged at 40 KG at 4° C. to separate the supernatant. The concentration of proteins in the obtained supernatant was determined by the BCA assay. To 10 μg of the protein amount, a phoresis buffer (0.6125 M Tris-HCl pH 6.8, 10% SDS, 50% glycerol, 0.02% bromophenol blue) and DTT with a final concentration of 50 mM were added, and heated at 65° C. for 20 minutes. Then, the sample thus prepared was loaded onto 10 to 20% polyacrylamide mini-gel and allowed to migrate by 30 mA C. C. (constant current).

A voltage of 40 V was applied for 1 hour to the gel, which had been subjected to SDS-PAGE above, with a transfer buffer (2 mM $CaCl_2$-containing 10 mM CAPS/10% methanol), and proteins derived from each sample were transferred to a PVDF membrane. Then, the membrane, on which the proteins was transferred, was immersed in a 2.5% glutaraldehyde solution for 1 hour, and then washed with PBS for 5 minutes. This washing operation was repeated three times (but, in the third time, the washing was performed with PBS to which monoethanolamine was added to a concentration of 50 mM). Subsequently, a blocking treatment was performed with a 5% skim milk solution for 1 hour. Thereafter, the membrane was gently rinsed with PBS, and then allowed to react with each primary antibody at room temperature in a moisture chamber for 2 hours. Note that the primary antibodies used are as follows.

An anti-metallothionein antibody (manufactured by Dako, product number: M0639, mouse-derived monoclonal antibody) is an antibody capable of recognizing 5 to 7 amino residues from the N-terminus of a metallothionein protein, and binds to all the isoforms of MT-1 and MT-2. Moreover, when used in this western blotting, the antibody was diluted to 1/100 with 0.1% BSA/PBS for use. An anti-actin antibody (manufactured by Sigma-Aldrich Co, product number: A2103, rabbit-derived polyclonal antibody) is an antibody used to detect actin as an internal standard in each sample. When used in this western blotting, the antibody was diluted to 1/500 with 0.1% BSA/PBS for use.

The membrane having reacted with each primary antibody as described above was washed with a PBS solution containing 1% skim milk and 0.1% Tween 20 for 5 minutes. After this washing operation was repeated three times, the membrane was further gently rinsed with PBS. Then, the membrane was allowed to react with secondary antibodies corresponding to the primary antibodies at room temperature in a moisture chamber for 30 minutes. Note that the secondary antibodies used are as follows.

A goat-derived anti-mouse IgG antibody (manufactured by Thermo Fisher Scientific Inc., #31432) was diluted to 1/10000 with 0.1% BSA/PBS for use to detect the anti-metallothionein antibody.

A goat-derived anti-rabbit IgG antibody (manufactured by IBL CO., LTD., #17502) was diluted to 1/2000 with 0.1% BSA/PBS for use to detect the anti-actin antibody.

The membrane having reacted with each secondary antibody as described above was washed with a PBS solution containing 1% skim milk and 0.1% Tween 20 for 5 minutes. After this washing operation was repeated three times, the membrane was further gently rinsed with PBS. Then, the membrane was allowed to react with SuperSignal (registered trademark) West Pico Chemiluminescent Substrate (manufactured by Thermo Fisher Scientific Inc.) at room temperature for 1 minute. Subsequently, the exposure and development processing was performed in a dark room, and the metallothionein protein and the actin protein were detected.

<Immunostaining>

First, each peripheral nerve specimen was fixed with 10% formalin and then embedded with a paraffin. Then, after each peripheral nerve specimen was sliced into thin sections, the paraffin was removed. The resultant was immersed in 3% $H_2O_2$ methanol for 10 minutes, followed by washing with PBS for three minutes. After this washing operation was repeated three times, an antigen activating solution (pH 9, manufactured by Nichirei Corporation) was added thereto and autoclaved at 105° C. for 15 minutes. Then, after residual heat was dissipated, the resultant was washed with PBS for three minutes. After this washing operation was repeated three times, two drops (approximately 100 μL) of a blocking reagent (BLOCK ACE, manufactured by Snow Brand Co., Ltd.) was placed on each section (slide). Subsequently, 100 μL of each primary antibody was placed thereon and allowed to react with each section for 1 hour. Note that the primary antibodies used are as follows.

An anti-metallothionein antibody (manufactured by Dako, product number: M0639, mouse-derived monoclonal antibody) is an antibody capable of recognizing 5 to 7 amino residues from the N-terminus of a metallothionein protein, and binds to all the isoforms of MT-1 and MT-2. Moreover, when used in this immunostaining, the antibody was diluted to 1/50 for use.

An anti-S100 antibody (manufactured by Dako, N1573, rabbit-derived polyclonal antibody) is an antibody capable of recognizing S-100A1 and B that are markers specific to Schwann cells. Moreover, when used in this immunostaining, the antibody was directly used at the same concentration as the time when provided from the manufacturing company.

An anti-NFM antibody (manufactured by Invitrogen Corporation, 13-0700, mouse-derived monoclonal antibody) is an antibody capable of recognizing the C-terminus of NFM that is a marker specific to an axon. Moreover, when used in this immunostaining, the antibody was diluted to 1/100 for use.

The sections having reacted with each primary antibody as described above were washed with PBS for three minutes. After this washing operation was repeated three times, 100 μL of secondary antibodies corresponding to the primary antibodies were placed on and allowed to react with each section for 30 minutes. Note that the secondary antibodies used were antibodies included in Envision (manufactured by DAKO ChemMate) universal kit.

The sections having reacted with each secondary antibody as described above were washed with PBS for three minutes. After this washing operation was repeated three times, 100 μL of a DAB coloring solution was placed on and allowed to react with each section for 10 minutes. Further, the nuclei were stained with hematoxylin, followed by dehydration and mounting. The observation was made under a microscope.

TABLE 3

|  | MT | S100 | NFM |
|---|---|---|---|
| CRPS1 | − | + | + |
| CRPS2 | − | + | + |
| CRPS3 | − | + | + |
| Control 1 | ++ | ++ | + |
| Control 2 | + | ++ | + |
| Control 3 | ++ | ++ | + |

TABLE 4

|  | The number of specimens | Average age | Male:female | Positive | Negative |
|---|---|---|---|---|---|
| CRPS | 5 | 52 ± 14.4 | 1:4 | 0 | 5 |
| Painful neuroma | 2 | 44.5 ± 13.4 | 1:1 | 0 | 2 |
| Fresh cadaver | 5 | 84 ± 7.1 | 3:2 | 5 | 0 |
| Benign tumor | 5 | 51 ± 16.4 | 2:3 | 5 | 0 |
| Malignant tumor |  |  |  |  |  |
| with decalcification | 11 | 28.6 ± 25.2 | 7:4 | 2 | 9 |
| without decalcification |  |  |  |  |  |
| with preoperative chemotherapy | 10 | 50.2 ± 15 | 4:6 | 10 | 0 |
| without preoperative chemotherapy | 26 | 64.7 ± 16.9 | 12:14 | 26 | 0 |

As apparent from the result shown in FIG. 1, in agreement with the proteomic analysis result, the MT protein was expressed in the normal nerves, while no expression thereof was observed in the peripheral nerves of the CRPS patients.

Additionally, as apparent from the result shown in FIG. 2 and Table 3, the result of evaluating the localization of MT by immunostaining showed that the expression of the MT protein was not observed in axons, but the MT protein was expressed in Schwann cells. Moreover, although unillustrated in the figure, as apparent from the result shown in Table 4, no expression of the MT protein was observed in all of the painful peripheral nerves (five CRPS specimens and two painful neuroma specimens); in contrast, the expression of the MT protein was observed in all of the 57 peripheral nerve specimens except for nine specimens whose tissue samples were decalcified.

Example 3

Experiment of Locally Administering MT Protein to Seltzer Model

From the above result, a MT protein was locally administered to a seltzer model having neuropathic pain (neurogenic pain) in order to examine whether or not the MT protein had an effect on pain of the model. FIGS. 3 to 6 show the obtained result. Note that the model rats used, the method for preparing the MT protein to be administered to the model rats, the method for evaluating the model rats, and so forth are as described below. Moreover, the Seltzer model is also called a partial sciatic nerve ligation (partial sciatic nerve injury, PSL) model, and construed as a model for neuropathic pain (see Sasaki et al., Folia Pharmacologica Japonica, 2006, vol. 127, pp. 151 to 155).

<Method for Preparing Seltzer Model>

The surgery for the partial sciatic nerve ligation model (Seltzer model) was performed on eight SD rats (female, body weight: 240 to 260 g). Specifically, the rats were anesthetized by intraperitoneally administering 50 mg/kg of pentobarbital sodium, and then placed in the prone position. A proximal portion of a right thigh of each rat was cut approximately 2 cm, and the sciatic nerve therebelow was exposed. Subsequently, 8-0 nylon was used to firmly ligate ⅓ to ½ of the sciatic nerve on the dorsal and distal side near a trochanter of the femur where the posterior biceps semitendinosus arose and branched. Then, the fascia and the skin were sutured with 4-0 nylon.

<Method for Preparing MT Protein>

First, total RNA was extracted from the peripheral nerve specimen using TRI Reagent (registered trademark, manufactured by Sigma-Aldrich Co.), and cDNAs were synthesized with Superscript Synthesis System (manufactured by Invitrogen Corporation). Then, using each of the obtained cDNAs as a template and the following primers, full-length human MT2A was amplified by PCR.

```
Sequences of primers
5'-GAAGATCTATGGATCCCAACTGCTCCTG-3'   (SEQ ID NO: 1)

5'-GGAATTCAGGCGCAGCAGCTGCACTTG-3'    (SEQ ID NO: 2)
```

Then, a plasmid (pGEX-6P-1, manufactured by GE Healthcare) was treated with restriction enzymes BamH1 and EcoR1, while the full-length human MT2A obtained by the amplification was treated with restriction enzymes Bgl2 and EcoR1. Subsequently, the plasmid and the full-length human MT2A were ligated to each other using Ready-To-Go T4 DNA Ligase (manufactured by GE Healthcare) to construct a plasmid vector capable of expressing the full-length protein of human MT2A. Thereafter, the obtained plasmid vector was introduced into *Escherichia coli* (BL21).

After that, this *Escherichia coli* was incubated in 2 mL of an LB medium containing 50 μg/ml of ampicillin and 0.2% glucose overnight while being shaken at 250 r/min at 37° C. Then, on the following day, 500 μL of the culture solution was added to 50 ml of an LB medium containing 50 μg/ml of ampicillin and 0.2% glucose, and further incubated overnight while being shaken at 250 r/min at 37° C. Subsequently, on the following morning, the OD of the culture solution was measured, and adjustment was made in such a manner that the OD600 became 0.1 after scale-up. After the adjustment, 10 mL of the obtained culture solution was added to 500 mL of an LB medium containing 1 mM $ZnSO_4$, and incubated while being shaken at 250 r/min at 37° C. until the OD600 became 0.8. Then, after such an incubation, a 0.1 M IPTG solution was added to a final concentration of 0.1 mM. The mixture was further incubated for 8 hours while being shaken at 250 r/min at 30° C. Then, the resulting culture solution was centrifuged at 5000 g at 4° C. for 15 minutes, and thereafter the supernatant was discarded to obtain only pellets. After that, the obtained pellets were washed with PBS, and then centrifuged at 4000 rpm at 4° C. for 20 minutes, and the supernatant was discarded. Subsequently, the resulting pellets were suspended in a lysis buffer (50 mM Tris-HCl pH 7.4, 0.25 M sucrose, 1% Triton X-100, 1 mM EDTA, 1 mM DTT, 1× Complete (protease inhibitor, manufactured by Roche Diagnostics Corporation, product number: 1873580), 1 mM PMSF), followed by ultrasonication. Thereafter, the resultant was centrifuged at 10000 g at 4° C. for 30 minutes, and then the supernatant was collected. Subsequently, to the collected supernatant thus obtained, a glutathione sepharose 4B gel (GS4B gel, manufactured by GE Healthcare) was added and subjected to a rotation treatment at room temperature for 1 hour. Thereafter, the GS4B gel mixture solution was centrifuged at 500 g at 4° C. for 5 minutes. After that, the supernatant was discarded, and the GS4B gel was collected. The collected GS4B gel thus obtained was washed with PBS, and then dispensed into a column, followed by washing with PBS and a prescission buffer (50 mM Tris-HCl pH 7.4, 150 mM NaCl, 1 mM EDTA, 1 mM DTT). Subsequently, after 1 mL of an enzyme solution (920 μL of a prescission buffer, and 80 μL of prescission protease) was added thereto, the resultant was left standing at 4° C. for 4 hours. Then, a prescission buffer was added to the column, and a recombinant human MT2A protein was collected.

<Administering MT Protein to Seltzer Model>

Immediately after the surgery, the metallothionein 2A recombinant protein (recombinant-Metallothionein 2A, rMT2A) was administered to the treatment group, while PBS was administered to the control group. Specifically, on the day of the surgery, 20 μg of rMT2A was diluted to 0.1 mL with PBS, and intraneurally administered to the sciatic nerve of the Seltzer model through a 27G needle pierced therein (0.1 ml of PBS was administered to the control group). Moreover, for 6 days thereafter, 10 μg of rMT2A diluted to 0.4 mL with PBS was transdermally and locally injected around the nerve everyday (the control group was locally injected with 0.4 mL of PBS).

<Evaluation of Seltzer Model Behavior>

The behaviors of the model rats were evaluated as follows by a von Frey test and a Hargreaves test before the surgery, and on Day 1, Day 3, Day 5 and Day 7 after the surgery.

—Von Frey Test—

A plastic case was installed on a mesh platform, and the model rats were placed in the case and left for 20 minutes until they had calmed down. Then, three types of stimuli of 1.26 g, 4.35 g, and 8.75 g were alternately applied to right and left hind paws ten times each with von Frey filaments (Semmes-Weinstein monofilaments: Stoelting Co. USA). This stimulus application was performed in three sets. The number of times of a withdrawal response (in this case, a behavior of raising the poked paw) was counted. Values were calculated as follows: a total number of times of the withdrawal response made to a stimulus to a left (unaffected side) hind paw was subtracted from a total number of times of the withdrawal response made to the stimulus to a right (affected side) hind paw.

Note that such numerical values as 1.26 g, 4.35 g, and 8.75 g were obtained by calibrations at each inspection time. In addition, 20 Von Frey Monofilaments were prepared according to the thickness of the diameter. Numbers (index numbers) were assigned thereto as 1.65, 2.36, ..., 6.45, 6.65 in an ascending order of the diameter. Hence, in FIGS. 3 to 5, the index numbers corresponding to the calibrated numerical values are also indicated (see the description of Judith Bell-Krotoski et al., THE JOURNAL OF HAND SURGERY, January, 1987, vol. 12A, no. 1, pp. 155 to 161 for the calibrated numerical values and the index numbers).

—Hargreaves Test—

A plastic case was installed on a glass platform, and the model rats were placed in the case and left for 20 minutes until they had calmed down. Then, using a model-390 apparatus for applying a thermal stimulation under unrestrained condition, (manufactured by IITC Life Science, USA), a thermal stimulation was applied to right and left hind paws to measure a period until a withdrawal response was made (period until the heated paw was raised). Note that the measurements were performed five times on both of the right and left sides to calculate an average period. Values were calculated as follows: an average period from when a thermal stimulus was applied on a right (affected side) hind paw until when the withdrawal response was made was subtracted from an average period of a left (unaffected side) hind paw.

Additionally, in both of the von Frey test and the Hargreaves test, the comparison was made on the right-left differences. In the statistical analysis, an unpaired Student's t test was employed with a significant difference of $P<0.05$.

As apparent from the results shown in FIGS. 3 to 6, in the von Frey tests with the stimuli of 4.35 g and 8.75 g, the pain behavior was significantly decreased from Day 3 after the surgery. Furthermore, with the stimulus of 1.26 g also, a significant decrease in the pain behavior was observed on Day 7 after the surgery. Normally, in a von Frey test, pain due to a stimulus applied using a Von Frey Monofilament with a larger diameter (in this Example, a stimulus applied using Von Frey Monofilament of 5.07 (8.75 g)) and pain due to a stimulus applied using a Von Frey Monofilament with a smaller diameter (in this Example, a stimulus applied using Von Frey Monofilament of 4.17 (1.26 g)) are different from each other not only in quantity but also in quality. Accordingly, neural circuits responding to these different stimuli are presumably different from each other. To put it differently, the primary sensory serve mainly consists of an Aβ fiber responsible for tactile sensation, an Aδ (delta) fiber responsible for acute pain, and a C fiber responsible for dull pain, and sensation of warmth and cold. It is believed that neurogenic pain causes complex nerve fiber response modulations such as changing a tactile sensation to strong pain. Thus, it was also revealed that the MT protein had an effect of suppressing both of different pains due to these different stimuli.

Figure 6:
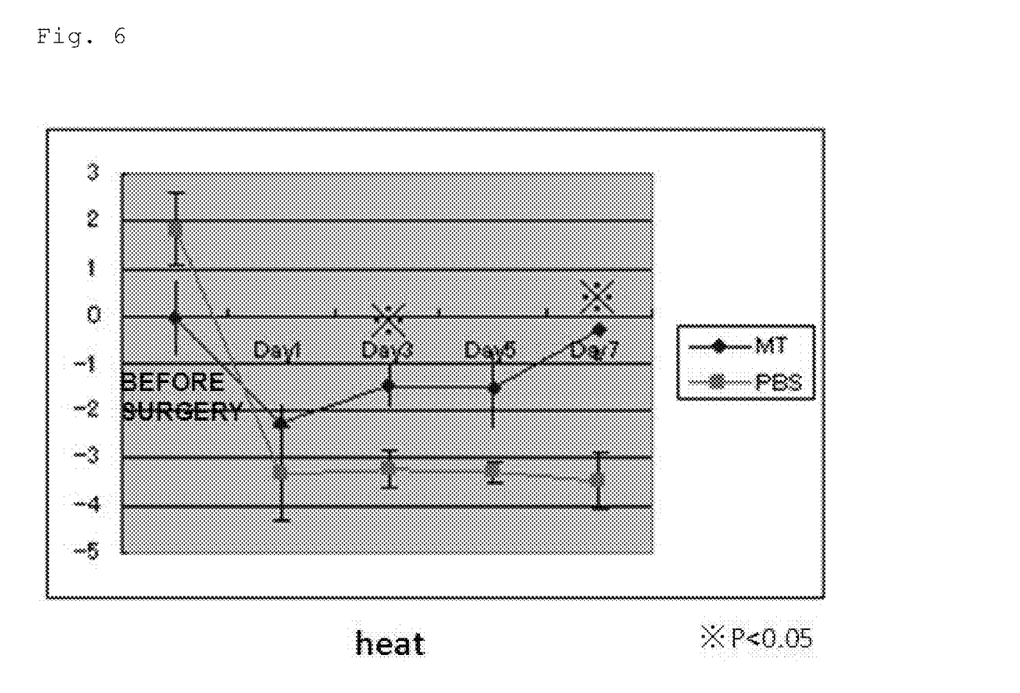
FIG. 6 shows a graph for illustrating the result of examining the effect of locally administering MT on pain of the Seltzer model by a Hargreaves test. Note that the horizontal axis shows the results on Day 1, Day 3, Day 5, and Day 7 after the day of the surgery for preparing the Seltzer model, and before the surgery. The vertical axis indicates a value obtained as follows: an average period from when a thermal stimulus was applied on a right (affected side) hind paw of the Seltzer model until when a withdrawal response was made was subtracted from an average period of a left (unaffected side) hind paw.
Figure 7:
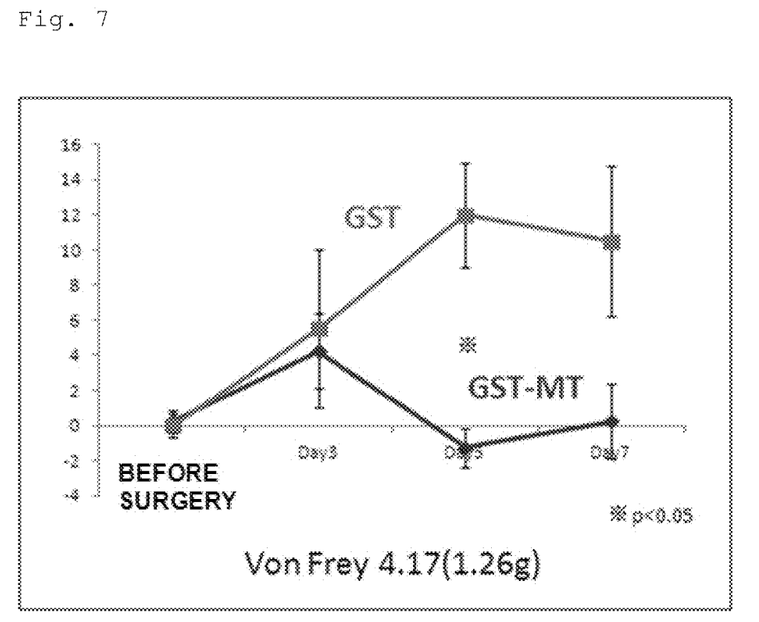
FIG. 7 shows a graph for illustrating the result of examining the effect of intraperitoneally administering a GST-fused MT protein (GST-MT) on pain of the Seltzer model by the von Frey test (stimulus: 1.26 g). Note that the horizontal axis shows the results on Day 3, Day 5, and Day 7 after the day of the surgery for preparing the Seltzer model, and before the surgery. The vertical axis is the same as that in FIG. 3.
Figure 8:
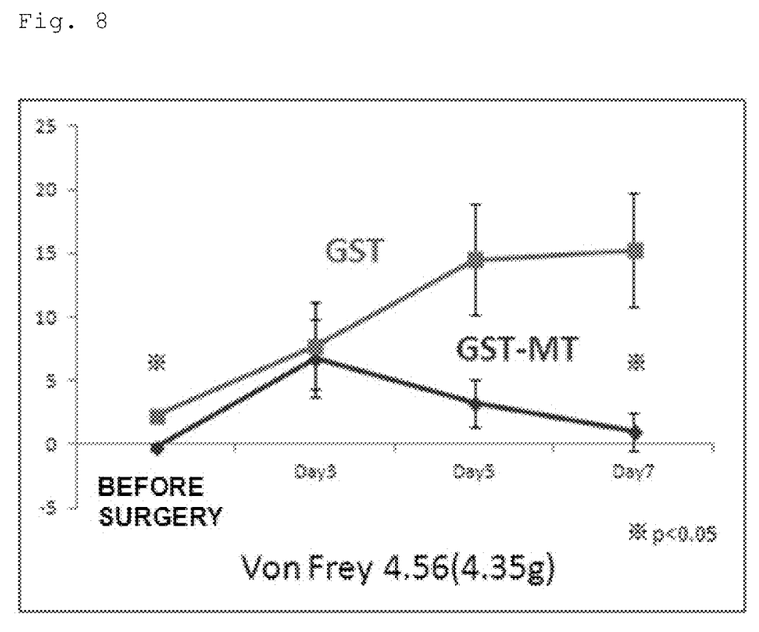
FIG. 8 shows a graph for illustrating the result of examining the effect of intraperitoneally administering GST-MT on pain of the Seltzer model by the von Frey test (stimulus: 4.35 g). Note that the horizontal axis shows the results on Day 3, Day 5, and Day 7 after the day of the surgery for preparing the Seltzer model, and before the surgery. The vertical axis is the same as that in FIG. 4.
Figure 9:
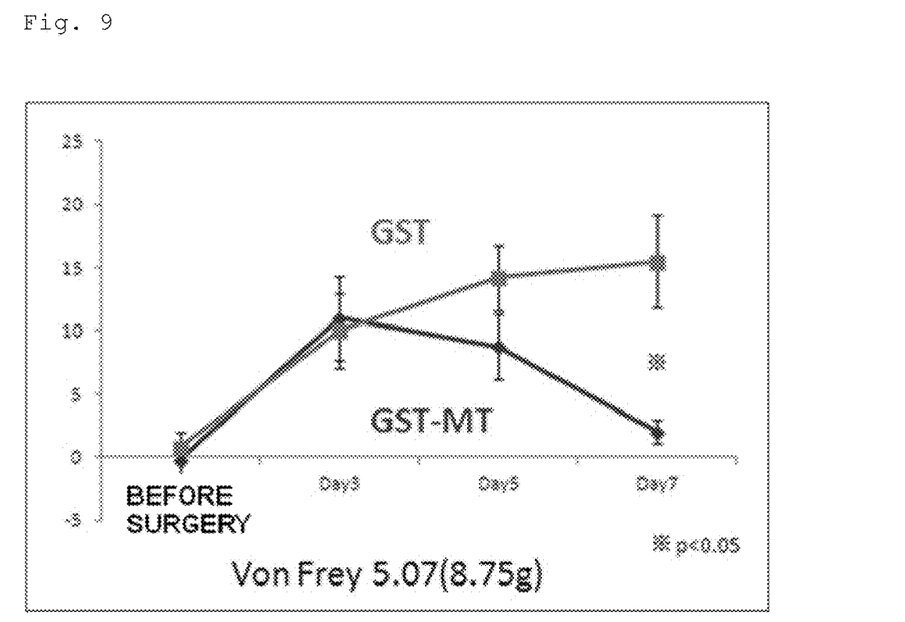
FIG. 9 shows a graph for illustrating the result of examining the effect of intraperitoneally administering GST-MT on pain of the Seltzer model by the von Frey test (stimulus: 8.75 g). Note that the horizontal axis shows the results on Day 3, Day 5, and Day 7 after the day of the surgery for preparing the Seltzer model, and before the surgery. The vertical axis is the same as that in FIG. 5.

Moreover, in the Hargreaves test, on Day 3 and Day 7 after the surgery, the periods until the withdrawal response were significantly improved. Thus, it was revealed that administering the MT protein to rats made it possible to significantly suppress pain for the rats. In addition, together with the result of the von Frey test, it was revealed that the MT protein had an effect of relieving pain corresponding to both of a mechanical stimulus and a thermal stimulus.

Example 4

Experiment of Intraperitoneally Administering MT Protein to Seltzer Model

On the day of the surgery as well as for the subsequent days, a GST-fused MT protein was intraperitoneally administered (IP) by 100 µg each time to the Seltzer model. Meanwhile, as the control group, a Seltzer model was also prepared, to which a GST protein was administered instead of the GST-fused MT protein. Then, as described in Example 3, the behaviors of these model rats were evaluated. FIGS. 7 to 10 show the obtained results. Note that the GST-fused MT protein administered to the Seltzer model is a recombinant human MT2A protein in <Method for Preparing MT Protein>, which still had GST remained attached thereto because no prescission treatment was performed.

As apparent from the results shown in FIGS. 7 to 10, in the von Frey test with the stimulus of 1.26 g, the pain behavior was significantly decreased from Day 5 after the surgery. Moreover, with the stimulus of 4.35 g or 8.75 g, a significant decrease in the pain behavior was observed on Day 7 after the surgery.

Figure 10:
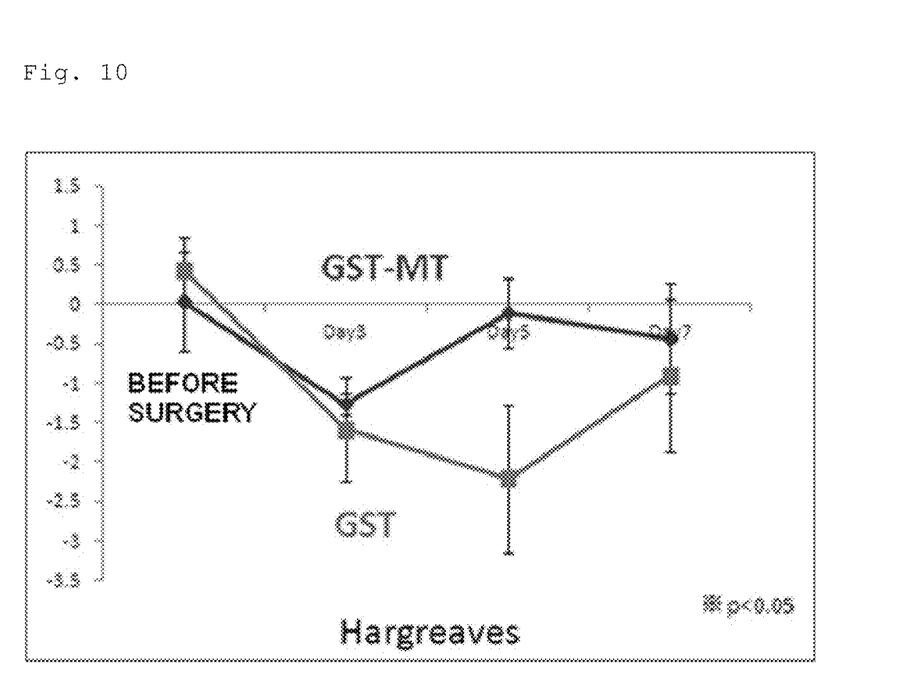
FIG. 10 shows a graph for illustrating the result of examining the effect of intraperitoneally administering GST-MT on pain of the Seltzer model by the Hargreaves test. Note that the horizontal axis shows the results on Day 3, Day 5, and Day 7 after the day of the surgery for preparing the Seltzer model, and before the surgery. The vertical axis is the same as that in FIG. 6.

Further, in the Hargreaves test, no statistically significant difference was observed, but the period until the withdrawal response was apparently improved as shown in FIG. 10.

Thus, it was revealed that the MT protein had an effect of relieving pain corresponding to both of a mechanical stimulus and a thermal stimulus, not only when locally administered as described in Example 3 (administered to the injured nerve and therearound) but also when intraperitoneally administered. Additionally, it was also revealed that the MT protein had a pain-improving effect even with a tag protein (GST) for purification still remained attached thereto.

INDUSTRIAL APPLICABILITY

The composition of the present invention comprising any one of a MT protein, a gene encoding the protein, and a vector in which the gene is inserted makes it possible to treat, improve, or prevent pain on the basis of a novel action mechanism. Moreover, the composition of the present invention comprising a molecule capable of detecting an expression of a MT protein makes it possible to diagnose pain with an objective indicator. Therefore, the present invention can greatly contribute particularly to the medical field.

[Sequence Listing Free Text]

SEQ ID NOs: 1 and 2

<223> Artificially synthesized primer sequence

The invention claimed is:

1. A method for treating, improving, or preventing pain, the method comprising administering any one of a full length metallothionein protein, a gene encoding the protein, and a vector in which the gene is inserted; excluding a method for treating, improving, and preventing, wherein the pain is due to heavy-metal poisoning.

2. A method for treating, improving, or preventing pain, the method comprising administering any one of a full length metallothionein protein, a gene encoding the protein, and a vector in which the gene is inserted; wherein the pain is any one of carpal tunnel syndrome, cubital tunnel syndrome, Guyon's canal syndrome, thoracic outlet syndrome, tarsal tunnel syndrome, Morton disease, CRPS, diabetic neuropathy, arm nerve injury, intercostal neuralgia (postherpetic neuralgia), carcinomatous neuropathy, painful neuromas, phantom pain, and post-surgery pain syndrome.

3. A method for treating, improving, or preventing pain, the method comprising administering any one of a full length metallothionein protein, a gene encoding the protein, and a vector in which the gene is inserted; wherein the pain is pain produced by any one of peripheral nerve injuries by trauma, phantom pain by amputation, radiculopathy by disc herniation, metabolic diseases, infections, tumor invasions, spinal cord injuries, stroke, and multiple sclerosis.

* * * * *